March 15, 1966 C. L. COOPER Plant Pat. 2,606

APPLE TREE

Filed Jan. 6, 1964

2 Sheets-Sheet 1

INVENTOR.
CALVIN L. COOPER

BY Reynolds & Christensen
ATTORNEY

Reynolds & Christensen

United States Patent Office

Plant Pat. 2,606
Patented Mar. 15, 1966

2,606
APPLE TREE

Calvin L. Cooper, Pateros, Wash.

Filed Jan. 6, 1964, Ser. No. 336,083
1 Claim. (Cl. Plt.—35)

This invention or discovery relates to a new and distinct variety of apple tree originating as a bud sport on a red delicious tree growing in my orchard near Brewster, Okanogan County, Washington. The parent spur-type red delicious variety is believed to be Starkrimson, Plant Patent No. 1565, although it also closely resembles Wellspur, unpatented (true parentage unknown).

Like its parent, the tree of this new variety is of semi-dwarf size, has an upright growth habit and spurred branches. Also, like its parent, it has an early bearing habit.

While the fruit of the parent tree colors with a blush, the fruit of my new variety colors with a distinct stripe.

Figure 1:
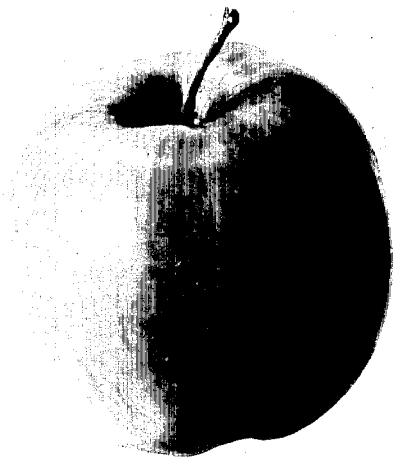
Figure 2:
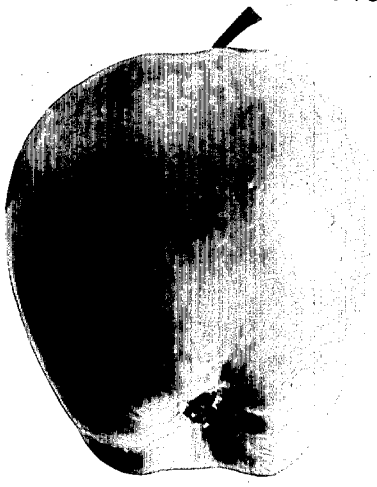
Figure 3:
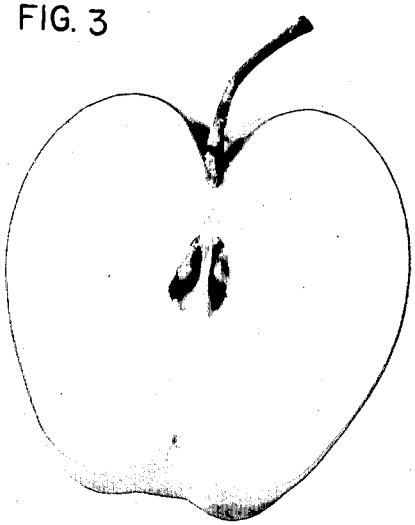
Figure 4:
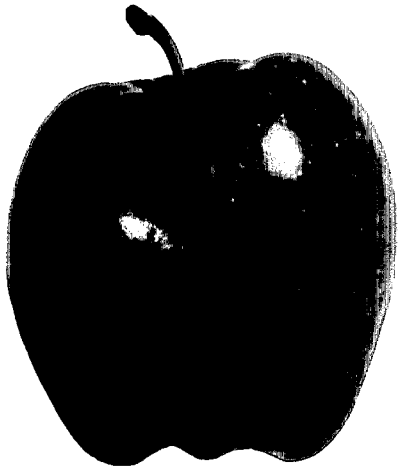

In the accompanying drawings FIGURES 1, 2 and 3 are top and bottom perspectives and a cross-sectional view respectively of a representative apple of the new variety picked 138 days after bloom, while FIGURE 4 is a side view of a representative apple of the new variety picked 152 days after bloom.

The following detailed description of the new variety outlines its general identifying characteristics:

*Tree.*—Semi-dwarf, upright, medium size, vase form, very productive. Trunk is of moderate stockiness. Branches are smooth with many spurs and medium thickness. Leaves are ovate, thick, of medium length and width and with margins coarsely serrated, and are colored approximately ivy green (Plate XXI, Ridgeway).

*Flowers.*—Pale pink to white, tinged with carmine (Plate I, Ridgeway).

*Fruit.*—Of generally uniform size, approximately 3⅜ inches axial diameter and 3⅛ inches transverse diameter. Of conical shape and ribbed. Cavity is symmetrical, rounded toward the apex and approximately ½ inch deep by 1¼ inches broad. The basin is symmetrical and approximately ⅜ inch deep and 1⅛ inches broad. The calyx is closed, broadly lanceolate and about ¼ inch long.

The skin is smooth, thick tough and of a waxy appearance, colored approximately Nopal red (Plate I, Ridgeway) with stripes of Bordeaux (Plate XII, Ridgeway). As the fruit reaches full color (approximately 152 days after bloom, depending on weather, etc.), the color becomes darker and more of an overall blush effect, but the striped pattern still remains visible as the lighter undertones. The core is small, with a bundle area of medium size, with the base acute and the halves slightly unequal. The flesh is juicy, firm, fine grained and crisp. It is colored creamy white, tinged with carmine (Plate I, Ridgeway) and sea-foam yellow (Plate XXXI, Ridgeway). The stem is long, brown and stout. The seeds are small with acute points and colored chestnut (Plate II, Ridgeway). The keeping quality is excellent.

*Comparison.*—The known varieties to which the presently described new variety is most similar are Starkrimson, subject of Plant Patent No. 1,565, and Starkspur, subject of Plant Patent No. 1,930. A principal difference between my new variety and Starkrimson is in the fruit of my new variety, which colors with a distinct stripe as depicted in the accompanying drawing, while fruit of Starkrimson colors with a predominant overall blush effect. A principal difference between my new variety and Starkspur is also in the fruit, which in my new variety achieves full color some ten to fourteen days earlier than the fruit of Starkspur and in the final stage of coloration at maturity has narrower and less pronounced stripes, with a more intense overall red blush background color than Starkspur. Moreover, the new variety may be readily distinguished from previously known striped spur-type red delicious in that there is a very pronounced pigmentation in the small applies of the new variety that drop from the tree of their own accord early in the season, i.e., at thinning time. These dropping fruits and their stems are colored a distinct red, which is not true of other striped spur-type red delicious. These comparisons are based on observations of trees growing in the same orchard area as that in which my new variety is grown.

The new and distinct variety of red delicious apple aforesaid orchard by means of buds and grafts and, based on comparisons of successive generation trees, its outstanding characteristics appear to be permanent.

Having thus disclosed this new variety of apple tree, I claim:

The new and distinct variety of red delicious apple tree, substantially as herein shown and described, characterized particularly by its production of fruit which colors some ten to fourteen days earlier than that of the Starkspur (Plant Patent No. 1,930) and with a color formation which is distinctly striped in comparison with the general blush coloration of Starkrimson (Plant Patent No. 1,565).

No references cited.

ABRAHAM G. STONE, *Primary Examiner.*

R. E. BAGWILL, *Assistant Examiner.*